(12) United States Patent (10) Patent No.: US 8,147,760 B1
Huvard et al. (45) Date of Patent: Apr. 3, 2012

(54) PORTABLE CHEMICAL OXYGEN GENERATOR

(76) Inventors: Gary Huvard, Chesterfield, VA (US); Richard Imbruce, Westport, CT (US); Kevin R. Ward, Glen Allen, VA (US)

( * ) Notice: Subject to any disclaimer, the term of this patent is extended or adjusted under 35 U.S.C. 154(b) by 0 days.

(21) Appl. No.: 13/197,782

(22) Filed: Aug. 4, 2011

(51) Int. Cl.
 *A62B 7/08* (2006.01)
 *A61M 16/10* (2006.01)
(52) U.S. Cl. .............. 422/120; 128/205.21; 128/202.26; 128/200.24; 422/261
(58) Field of Classification Search .................. 422/120, 422/188, 261; 128/200.24, 202.25, 202.26, 128/205.21; 252/186.43
See application file for complete search history.

(56) References Cited

U.S. PATENT DOCUMENTS

| | | | |
|---|---|---|---|
| 4,548,730 A | 10/1985 | Koslow | |
| 4,867,902 A | 9/1989 | Russell | |
| 5,431,022 A | 7/1995 | Abe | |
| 5,823,181 A | 10/1998 | Shih | |
| 6,267,114 B1 | 7/2001 | Ueno | |
| 7,171,964 B2 | 2/2007 | Moore et al. | |
| 7,407,632 B2 | 8/2008 | Ross | |

*Primary Examiner* — Sean E Conley
(74) *Attorney, Agent, or Firm* — Johan O. Brag; Innova Law, LLC

(57) ABSTRACT

A portable apparatus is provided which generates high purity breathable oxygen. The oxygen is produced in a reaction chamber from the reaction between an oxygen generating composition and a water/catalyst solution. The reaction chamber comprises a first compartment containing an oxygen peroxide adduct and a temperature stabilizing material formulated into controlled release tablets and a second sealed compartment containing a catalyst dispersed in an aqueous solution. The temperature stabilizing material undergoes an endothermic reaction upon dissolution in the solution. The tablets dissolve in the solution releasing hydrogen peroxide at a constant rate. The hydrogen peroxide is further decomposed into oxygen and water from contact with the catalyst. A first membrane made from a hydrophobic and gas permeable material, lets oxygen through while containing the reaction materials. A second membrane made of hydrophilic superabsorbent material and impregnated with catalyst particles absorbs any unreacted hydrogen peroxide letting high purity oxygen through.

12 Claims, 8 Drawing Sheets

PORTABLE CHEMICAL OXYGEN GENERATOR

This invention was made with government support under Grant # N000140710526 awarded by the Office of Naval Research. The Government has certain rights in the invention.

TECHNICAL FIELD

This application generally relates to portable chemical oxygen generating systems, particularly to systems which can produce oxygen of high purity for medical emergency situations.

DESCRIPTION OF THE RELATED ART

Oxygen generator systems capable of generating oxygen by decomposing hydrogen peroxide in the presence of a catalyst are well known in the art. U.S. Pat. No. 7,171,964 to Moore teaches an oxygen generation system which includes a reaction chamber that is partially filled with hydrogen peroxide of 7.5% in an aqueous solution. The portable oxygen generation system further includes a second chamber that is adjacent to the first chamber containing manganese dioxide powder acting as the catalyst. By breaking a seal between the two chambers, the hydrogen peroxide solution mixes with the manganese dioxide to produce oxygen which is released through an exit tube.

The chemical reaction that liberates oxygen is highly exothermic. It produces 23.4 kcal per mole of hydrogen peroxide (1938 cal/L $O_2$ produced). As a consequence of the large amount of hydrogen peroxide that might be present at the start of the reaction, the temperature in the reaction chamber will rapidly rise causing the aqueous solution of hydrogen peroxide to boil. The high reaction temperature typically requires some form of insulation in order for the system to be handled by a user safely. Since oxygen at a temperature greater than 50° C. will be harmful to a user, it also becomes necessary to cool and humidify the produced oxygen to make it breathable.

In order to reduce the safety risk associated with aqueous solution of hydrogen peroxide, solid hydrogen peroxide adducts such as sodium percarbonate and urea hydrogen peroxide have been used in chemical oxygen generator systems. U.S. Pat. No. 5,823,181 to Shih describes a system including a chemical module mounted in the reaction chamber containing a hydrogen peroxide and catalyzer. A plunger mounted on the reaction chamber to break the chemical module, enabling the two chemicals to mix with water, react and produce oxygen. Because of the large amount of oxygen produced, the chemical reaction is highly exothermic.

Various designs have been sought to protect the user from the heat generated by the exothermic reaction. Heat exchangers are often impractical and costly in portable units. In U.S. Pat. No. 7,407,632 to Ross, for instance, the reaction chamber is enclosed in an exterior housing creating an "air insulator" to prevent the heat from reaching the outer surface of the generator and allow safe handling. Such design does not prevent the reaction chamber from reaching high temperature.

Other designs seek to control the temperature inside the reaction chamber by capturing part of the heat generated in the reaction. In U.S. Pat. No. 4,548,730, Koslow teaches how heat-absorbing hydrated salts can be intermixed with oxygen-generating materials to absorb excessive heat released upon exothermic chemical decomposition of hydrogen peroxide. A limitation with such hydrated salts is that they release carbon dioxide upon heating.

As a consequence of the high thermal energy produced by the chemical reaction, current chemical oxygen generation devices are more hazardous than alternative sources of oxygen production. There is therefore a need for a portable oxygen generation system capable of controlling the temperature of the reaction and providing a safe delivery of oxygen to the user.

Another common problem involves the removal of solid particles or liquids from the produced oxygen flow. Shi teaches a filter device comprising active carbon or active aluminum for removing solid matter from air passing through. Moore suggests a hydrophobic filter inline with the oxygen release tube to capture any undesirable liquid or chemicals. Alternatively, Ross suggests a membrane stack comprised of multiple replaceable components to filter out chemical impurities and break any foam produced from the reaction.

A different approach to the problem of capturing any excess liquid, foam or chemical impurities resulting from the reaction is taught by Ueno in U.S. Pat. No. 6,267,114. In one embodiment, the chemical reaction occurs in an inner bag made of a watertight sheet material or membrane which prevents water from flowing and gas permeable so to allow oxygen to pass through.

Furthermore, the elevated temperature may cause some of hydrogen peroxide to vaporize and mix with the oxygen generated by the reaction. Since aspiration of hydrogen peroxide is toxic, there is a need to filter out any residual hydrogen peroxide vapors from the produced oxygen gas before it is supplied to the user. Current devices have failed to provide a solution to this problem. There is therefore a need for a portable system capable of producing oxygen free of water and hydrogen peroxide vapors, bacteria and other contaminants.

Another common problem with existing chemical oxygen generators is the inability to control the rate of oxygen production during operation. The exothermic reaction is generally a runaway chemical reaction, meaning that the rate of oxygen production at any point in time is strictly controlled by the amount of reactants in the system. While the total oxygen yielded can easily be determined from the quantities of oxygen producing chemicals, the rate of oxygen production is not constant and will rapidly decrease over time as the reactants are consumed. The rate of oxygen production is a direct function of the amount of hydrogen peroxide in solution. This results in an unpredictable oxygen flow as well as uncertain and variable duration of oxygen production.

For systems that use solid hydrogen peroxide adducts such as sodium percarbonate, the actual peroxide content in the solid reactant may vary considerably resulting in variable oxygen flows. Adding more reactants at the initiation of the reaction will not increase the duration of oxygen production; it will just increase the rate of oxygen production.

Attempts to control the rate of oxygen production reaction have been reported in the literature, although these attempts have been only partially effective or are technically cumbersome. U.S. Pat. No. 7,465,428 to Ross discloses a method to control the rate of oxygen production by providing mechanical means to release solid reactants over time. Again such solutions will not eliminate the wide swings in oxygen production. Each successive release is followed by a sudden increase in the rate of oxygen production. Such an approach also fails to prevent the reaction from running out of control.

Other methods have use coatings of the oxygen generating compounds to slow down the chemical reaction. U.S. Pat. No. 4,867,902 to Russell discloses a means to slow the oxygen producing reaction by means of micro-encapsulation of the oxygen generation compounds in a wall-forming polymer coating swellable in water. As soon as the external coating is dissolved, the reaction will run away and oxygen production will rapidly increase to a peak and then rapidly decrease as the chemical compounds are fully reacted. While a slowly dissolving coating may delay the reaction, it does not provide a means of controlling the rate of oxygen production.

Because of the above mentioned problems, currently available chemical oxygen generation systems are highly inefficient compared to alternative sources of oxygen such as pressurized gas canisters. Current systems produce much more oxygen during the early phase of the chemical reaction than in the later phase, resulting in much of the produced oxygen being wasted. This makes chemical oxygen generation systems as presently produced ill-suited for use in life support or rescue operations where a relatively constant flow and reliable flow of oxygen is desired. There is therefore a need for a portable system capable of producing a predictable and constant flow of oxygen for an extended period of time.

SUMMARY

The present device relates to a chemical oxygen generation system which can produce oxygen free of hydrogen peroxide and other contaminants at a controlled flow and temperature over an extended period of time. In an embodiment of the inventive subject matter, the present device can generate a constant flow of oxygen of 3 L/min at a temperature of less than 45° C. for more than 30 minutes.

In the present device, oxygen is generated chemically from the catalytic decomposition of hydrogen peroxide by a catalyst such as manganese dioxide ($MnO_2$) to yield water and oxygen. Hydrogen peroxide is produced from the slow decoupling of a hydrogen peroxide adduct such as urea hydrogen peroxide (UHP). The hydrogen peroxide adduct (a solid) is formulated into controlled release tablets which dissolve slowly in water and release hydrogen peroxide at a constant rate thereby controlling the rate of release of hydrogen peroxide to an $MnO_2$-containing aqueous solution.

The present device contains two main chemical reactants: the oxygen producing chemicals formulated as controlled-release tablets and the catalyst-containing aqueous solution. The two reactants are isolated from each other until the device is activated. An activation mechanism combines the two reactants resulting in the instantaneous production of oxygen.

The controlled release tablets comprise a hydrogen peroxide adduct such as urea hydrogen peroxide UHP, sodium percarbonate or calcium peroxide, one or more hydrophobic binders such as crystallized sucrose, optionally a non-volatile hydrophobic oil, optionally a finely ground (200 mesh) clay (bentonite, atapulgite, kaolin) and one or more lubricants (e.g., stearic acid, magnesium stearate). The final controlled release tablets of the device herein will preferably contain about 1.57 gram of UHP adduct in an approximate 2 gram tablet. Thus, UHP adduct accounts for about 78.5% of the total tablet weight. More preferably the UHP accounts for 98% of the tablet weight. None of the tablet ingredients contains or can generate volatile organic compounds that could contaminate the oxygen. The hydrogen peroxide generated from the controlled release tablets is reacted quickly and instantly decomposed to water and oxygen; thorough testing has demonstrated the ability of the device to render pure oxygen containing no hydrogen peroxide residuals.

Manganese dioxide is used as an oxidizing reagent in many reactions in inorganic and organic chemistry and also as a catalyst for redox processes such as the decomposition of peroxides. The following redox cycle accounts for the manganese-induced peroxide decomposition:

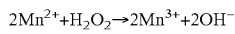

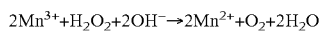

The manganese dioxide is commonly present in the form of a fine powder which is not soluble in water and will deposit at the bottom of a solution. A colloidal form of manganese dioxide (obtained by reduction of potassium permanganate with manganese sulfate) can preferably be used as it will remain dispersed evenly throughout the solution. The greater surface area of the colloidal nanoparticles will also provide faster decomposition rate of the hydrogen peroxide than with the powdered form.

In an embodiment of the inventive subject matter, the aqueous solution comprises a mixture of colloidal nanoparticles of $MnO_2$ and powdered (5-10µ) $MnO_2$ dispersed in water. With the exception of the water, the components of the aqueous solution are nonvolatile and contain either zero or acceptably low levels of residual volatile organic compounds (VOCs).

The controlled release tablets and the aqueous solution are isolated from each other prior to activation. In an embodiment of the inventive subject matter, the aqueous solution is contained in a sealed watertight bag. An activation mechanism ruptures the sealed watertight bag releasing the aqueous solution. The aqueous solution then contacts and submerses the controlled-release tablets. The activation mechanism may comprise a cord or safety pin attached to the side of the sealed watertight bag which cord or safety pin releases the contents of the sealed watertight bag when pulled. In some embodiments, the user may physically squeeze the sealed watertight bag in order to activate the mechanism by breaking a frangible seal. Alternatively, the activation mechanism may comprise a handle or knob which when turned opens a valve releasing the contents of the sealed watertight bag.

On contact with the aqueous solution, the controlled release tablets begin to dissolve. When the tablets dissolve, the released UHP decouples instantly to urea and hydrogen peroxide. The hydrogen peroxide further decomposes to water and oxygen upon contact with the $MnO_2$ catalyst particles. The decomposition rate of hydrogen peroxide depends on the concentration of the hydrogen peroxide and on the reaction temperature. The chemistry of this device is designed to overwhelm the hydrogen peroxide with an overabundance of $MnO_2$. The very high surface area of the colloidal form of the catalyst ensures rapid and complete decomposition of the hydrogen peroxide upon release.

One aspect of the inventive subject matter is to contain the reaction materials inside the reaction chamber while allowing the produced oxygen through. In an embodiment of the inventive subject matter, the oxygen producing chemicals and aqueous solution chemicals are retained in the reaction chamber by a dual membrane filter: a first membrane made of a gas permeable and hydrophobic liquid impermeable material such as Tyvek® (Dupont, Wilmington, Del.) lets the produced oxygen through as well as any water and hydrogen peroxide vapors; a second membrane made of a hydrophilic superabsorbent material impregnated with catalyst particles lets the oxygen through while decomposing and absorbing any residual hydrogen peroxide vapors.

Another aspect of the inventive subject matter is to control the temperature of the highly exothermic chemical reaction. Excessive heating can lead to autocatalytic decomposition of hydrogen peroxide and a runaway chemical reaction. It can also lead to boiling of the liquid solution with water vapor and hydrogen peroxide vapor mixing with the produced oxygen.

Also, if the temperature rises too rapidly the decomposition of hydrogen peroxide accelerates leading to uneven oxygen production flows.

Various means are provided in the claimed inventions to control the temperature of the reaction. In one embodiment, the aqueous solution acts as a heat sink and absorbs some of the heat produced by the reaction. It is known that the enthalpy of the decomposition reaction of hydrogen peroxide is 46.8. kcal per mole of oxygen produced or 1.95 kcal per liter of oxygen produced at 20° C. In a system designed to generate 6 liters of oxygen per minute, the system will produce 11.7 kcal per minute. This is the amount of energy required to raise the temperature of one liter of water by 11.7 degrees per minute. A system producing 6 liters of oxygen per minute per minute and activated at ambient temperature of 20° C. would bring one liter of to a boil in less than seven minutes. A device strictly using water as a heat sink would therefore require large amounts of water, significantly adding to the weight of the device.

In another embodiment of the inventive subject matter, the reaction temperature is controlled by the addition of temperature stabilizing materials comprising phase change materials (PCM) with a melting temperature between 30° C. and 50° C. Phase change materials may be repeatedly converted between solid and liquid phases and utilize their latent heat of fusion to absorb, store and release heat or cool during such phase conversions. These latent heats of fusion are greater than the sensible heat capacities of the materials. For example, in phase change materials, the amount of energy absorbed upon melting or released upon freezing is much greater than the amount of energy absorbed or released upon increasing or decreasing the temperature of the material at an increment of 1° C. As the reaction temperature rises to the melting point of the particular PCM used, the PCM starts melting and the reaction mixture continues to maintain the inner temperature at the melting point until the PCM is fully melted. Thereafter, the added mass of the PCM also absorbs the released heat in the form of sensible heat. PCMs can be paraffin waxes or fatty acid esters from natural oil and fats such as coconut oil, palm kernel oil, margarines or cocoa butter which will undergo phase change transitions in the range of 20° C. to 60° C. Inorganic salts are not recommended as PCMs in the device as they produce carbon dioxide when heated. Phase change materials absorb heat when the material melts or undergoes some other endothermic phase change. Judicious choice of the phase change material and the amount used allows for control of the maximum temperature increase. That is, the device is configured so the contents cannot warm above a predetermined, calculable, safe temperature regardless of how quickly the chemical reaction proceeds.

PCMs are generally formulated to have sharp phase transition temperatures. This means that a thermal energy storage device comprised of a PCM will absorb little to no heat below the phase transition temperature, then rapidly absorb heat as the temperature reaches the phase transition temperature. Such a thermal energy storage device will not provide a means to absorb energy over a broad range of temperatures. We discovered that by mixing PCMs with different phase transition temperatures we could design a thermal energy storage device with a broad heat absorption behavior over a wide temperature range. In another embodiment, the temperature stabilizing materials comprise two or more PCMs with different phase change temperatures. A first PCM with a low melting temperature preferably in the range 20° C. to 30° C. is mixed with a higher melting temperature PCM preferably in the range 40° C. to 60° C. When mixed together these PCMs will exhibit a broad melting behavior over a wide 25° C. to 50° C. range unlike formulations from a single PCM with a sharp melting temperature. Additional PCMs with intermediate melting temperatures can be added to further control the absorption of energy over a broad range of temperatures. This ensures a gradual increase in temperature and an improved control over the rate of reaction.

We also discovered that because of the poor thermal conductivity of most PCMs, there was a lag between the time the reaction temperature reached the phase transition temperature and the time the PCM was able to absorb the heat generated. We discovered that by increasing the surface area of the PCM we could reduce this lag time. In another embodiment, the temperature stabilizing materials comprise a plurality of micro-encapsulated PCMs with different phase change temperatures in the range of 20° C. to 60° C. The high surface area of the microcapsules of PCM will provide shorter response time to increases in temperature as compared to solid blocks of PCMs and therefore better temperature control.

In another embodiment of the inventive subject matter, the temperature stabilizing materials comprise highly water soluble hydrophilic non-toxic organic compounds which dissolve endothermically in water. The endothermic dissolution reaction will absorb all or part of the excess energy produced during the exothermic chemical decomposition of hydrogen peroxide. Urea is a preferred material for such an application. Urea is non-toxic, has a solubility of 121 g per 100 ml of water at 25° C. and 164 g per 100 ml and 40° C. and an enthalpy of solution of 57.8 cal/g. Urea formulated in tablet, pellet or loose crystal form can be added to the UHP controlled release tablets as a temperature stabilizer. In an embodiment of the inventive subject matter, urea is mixed with UHP and pressed into tablets. Urea will dissolve simultaneously with the release of hydrogen peroxide in the aqueous solution. By adjusting the weight ratio between urea and UHP in the tablet composition it is possible to control the temperature of the aqueous solution to the desired level. Other materials which may be used as temperature stabilizing materials by dissolving endothermically in water include various inorganic and organic salts such as ammonium nitrate, magnesium chloride, sodium chloride and others which are known to those skilled in the art.

When oxygen is produced by the reaction of hydrogen peroxide with manganese dioxide particles in an aqueous solution, the oxygen will be saturated with hydrogen peroxide vapor and water vapor at the temperature of the reaction mixture. The reaction is catalyzed by the manganese dioxide from the water/catalyst mixture and the judicious choice of particulate size and amount of catalyst prevents the buildup of hydrogen peroxide in the suspension. There will be a finite, albeit small, concentration of hydrogen peroxide in the solution in order to maintain the rate of the chemical reaction and the concomitant production of oxygen. Hydrogen peroxide, like water, exerts a finite vapor pressure over the solution and will therefore be present at a low concentration in the oxygen that forms. Inhaling hydrogen peroxide over an extended period of time can cause irritation and, potentially, long term damage to the lungs.

Thus, a further aspect of the device is to remove residual hydrogen peroxide from the oxygen prior to the delivery to a user. Separation methods involving micro-filtration, diffusive separation or molecular sieves are not effective or practical. Water, hydrogen peroxide, and oxygen cannot be easily separated using microporous membranes. The molecular radii of water and hydrogen peroxide are too close for available membranes to separate. Hydrogen peroxide and oxygen have molecular sizes that differ by only two hydrogen atoms; far too little for a microporous membrane separation. It would be impossible to specify a membrane with a pore size such that hydrogen peroxide would be captured and oxygen would pass through. Diffusive separation of oxygen from water and hydrogen peroxide using nonporous polymer membranes is physically possible but the oxygen flux (mols/min/cm$^2$) is many orders of magnitude too low for an oxygen generation device with a flow rate up to 6 liters per minute and given a membrane surface area of 1000 cm$^2$ surface that is typically available in our device. Molecular sieves might be used to adsorb water vapor and hydrogen peroxide from the oxygen. However, they add undesirable weight and do not destroy adsorbed hydrogen peroxide. If limited to the above approaches, there is a potential for hydrogen peroxide to escape the device.

To overcome these limitations, we discovered that a second membrane capable of chemically decomposing any residual hydrogen peroxide would provide a solution to the unresolved problem of hydrogen peroxide abatement. In an embodiment of the inventive subject matter, the second membrane is made from a superabsorbent material capable of absorbing up to 800 times its dry weight in water. In an embodiment of the inventive concepts, the second membrane is made of a polypropylene melt-blown nonwoven fabric able to absorb at least 100 times its dry weight in water and that is impregnated via the well known needle-punch method with small polyacrylamide fibers, 5-10μ $MnO_2$ powder, and (optionally) activated carbon powder. Other non-woven or woven fabrics might be used. These include polyethylene, nylon, polyesters, poly(lactic acid), fiberglass, and natural fibers such as cotton and wool. Others will occur to those skilled in the art.

Polyacrylamide is a well known hydrophilic polymer in the art. It rapidly absorbs water vapor and any hydrogen peroxide vapor that might escape from the gas permeable reaction chamber that produces oxygen. Absorbed hydrogen peroxide and gaseous hydrogen peroxide will contact with the small particles of $MnO_2$ (high surface area, high capture efficiency) and will be catalytically converted into water and oxygen. Most of the water will remain absorbed and a negligible amount may escape with the oxygen. Thus, the oxygen is hydrogen-peroxide free and sub-saturated with water vapor upon delivery. Additionally, should the reaction chamber containing the oxygen-producing chemicals be compromised for any reason, the mixture in the reaction chamber will be absorbed by the superabsorbent material, preventing the inhalation of the mixture by the patient. In repeated testing of oxygen produced in prototype devices, no hydrogen peroxide was detected in the oxygen effluent. In an embodiment of the inventive subject matter, the amount of superabsorbent material used is calculated so as to absorb all of the aqueous mixture in the reaction compartment.

Optionally, the superabsorbent material can be impregnated with activated carbon powder to adsorb residual volatile organic compounds if those are found to be present in any of the construction materials or chemicals used. The optional activated carbon powder is used to adsorb any traces of volatile organic chemicals (VOCs) that might be present as impurities in the various components used to construct the device. For example, certain grades of polyethylene can contain residual solvents that are used as diluents in the manufacturing process (e.g., toluene, cyclohexane etc.). Trace amounts of some VOCs may be given off by certain antifoams used to control foam formation during the chemical reaction. For example, acetaldehyde has been detected in Pluronic L81-based antifoam, and siloxane monomers have been detected in polydimethylsiloxane antifoam. Both compounds can be effectively removed from the effluent oxygen by activated carbon.

If the superabsorbent membrane is not present, hydrogen peroxide vapor, as well as water vapor, will be found in the oxygen effluent at unacceptably high levels. We have tested for the presence of hydrogen peroxide in the oxygen produced in devices when the superabsorbent membrane was omitted or included. This was done by bubbling the effluent oxygen through an acidic solution of ferrous ammonium thiocyanate. Hydrogen peroxide oxidizes ferrous Fe(II) ions to ferric Fe(III) ions in an acidic solution, and ferric ions bind with thiocyanate ions to form a deep red complex. This complex has strong absorption at wavelengths of 450 nm and 560 nm. Thus, the colorimetric absorbance of the oxygen-treated solution at either wavelength can be measured to test for the presence of hydrogen peroxide in the oxygen. When a gas passes through a ferrous ammonium thiocyanate solution, hydrogen peroxide at 1 ppm in the oxygen can be detected. At these levels, the color change of the ferrous thiocyanate solution is not visually observable but it can be measured with a spectrometer. The oxygen from a device without the superabsorbent membrane causes visually observable red color when bubbled through ferrous ammonium thiocyanate solution. By contrast, when a $MnO_2$-impregnated superabsorbent membrane is used, no red color is observed visually and the absorbance change on a spectrometer is below the detection limit of the instrument. Other hydrophilic materials that might be used include various water soluble polymers. Hydrophilic powders can be used in combination with or in lieu of hydrophilic fibers. These include cross-linked polyacrylic acid (Carbopol® or generically, carbomers), starches and starch derivatives (Reon™), some flours, some quaternary salts, highly deacetylated chitosan and its hydrophilic derivatives. Any fibrous or powdered hydrophilic material that will absorb or adsorb 20-100× its own weight of water might be used. Other hydrophilic materials will occur to those skilled in the art. The reaction chamber and the hydrophilic enclosure are contained in an impermeable and pressure tight housing equipped with an overpressure vent to prevent a housing rupture in the event the oxygen outlet is occluded. The housing acts as temporary storage compartment for the produced oxygen. A flexible tube is attached at one end to the oxygen outlet and at the other end to a breathing apparatus.

Another aspect of the inventive subject matter is to control the rate of oxygen release at a level in order for it to remain constant during the reaction. This is generally referred to as a zero-order kinetics. Multiple variables affect the oxygen release rate: the temperature of the solution, the rate of dissolution of hydrogen peroxide and the amount of catalyst dispersed in the solution. The catalyst can be eliminated as a variable by ensuring that any hydrogen peroxide dissolved is immediately decomposed into oxygen and water. A catalyst such as manganese dioxide in insoluble in water and will deposit at the bottom of the aqueous solution. We discovered that by using a colloidal form of manganese dioxide, the catalyst particles remain suspended in the solution and do not deposit. Such a colloid can be produced by mixing a solution of manganese sulfate in a 7.2 pH phosphate buffer with a solution of potassium permanganate ($KMnO_4$) in a 7.2 pH phosphate buffer in stoichiometric ratio at a temperature between 60 and 70° C. Production of oxygen occurs at the surface of the catalyst and a colloidal form of manganese dioxide has a larger total surface area than a similar amount by weight of a coarser ground catalyst. With a large enough amount of the manganese dioxide dissolved in the solution, the rate of oxygen production will be controlled by the dissolution rate of hydrogen peroxide and by the reaction temperature. If too large a quantity of hydrogen peroxide adduct is dissolved at once in the aqueous solution, the rate of oxygen production will increase rapidly and uncontrollably. It is therefore an aspect of the inventive subject matter to control the rate of dissolution of the hydrogen peroxide contained in the UHP tablets in order to produce oxygen at a controllable and selectively constant rate.

In an embodiment of the present inventive subject matter, the rate of dissolution of urea hydrogen peroxide adduct in an aqueous solution is determined by specially formulated controlled-release tablets. The composition, shape and hardness of the tablets is adjusted to achieve a specified and constant tablet dissolution rate and thereby achieve a specified and zero-order (constant) release rate of oxygen. The use of gel forming agents to delay the release of drugs is well known in the art. The gel forming compounds are typically hydrophilic materials such hydroxypropyl methyl cellulose (HPMC), starches, flours, gums, or clays. The gel first acts to facilitate the penetration of the dissolution medium (water) into the tablet core (hydration). Second, the gel swells the tablet and finally helps transport the dissolved compound to the dissolution medium. The hydration and swelling eventually leads to the tablet disintegrating and a sudden increase in the dissolution rate. Such gel forming agents are therefore undesirable if the goal is to achieve a constant release rate.

We have discovered that mixing the hydrogen peroxide adduct with a hydrophobic, slowly dissolving binder provides high resistance to tablet erosion. In an embodiment of the inventive subject matter, crystallized sucrose with an agglomerated median particle size of 300 µm is used as binder. Crystallized sucrose has a large capacity to bind to water and thereby restrict its mobility and diffusion into the tablet. Crystallized sucrose is also a hard and not easily friable material, helping to maintain the shape of the tablet while it slowly dissolves. Other slowly dissolving inert solids known to those skilled in the art might be substituted for the crystallized sucrose. These include, but are not limited to, slow to dissolve sugars such as Sugartab® (JRS Pharma, Rosenberg, Germany), table sugar, table salt and other water soluble organic compounds and such fillers are included herein by reference to function. We have also discovered that mineral oils may be used to restrict diffusion of water into the tablet.

In an embodiment of the inventive subject matter, the tablets are in the shape of a disc having a ratio of tablet length to thickness ratio of 8:1 or greater to produce a zero-order release rate of oxygen. The rate of dissolution is directly proportional to the tablet surface area. The surface area is given by the formula:

$$A=2\pi r(r+h) \text{ where } r \text{ is tablet radius and } h \text{ is tablet thickness.}$$

For this aspect ratio, the dissolution of the tablets occurs predominantly on the two flat surfaces; the contribution of dissolution around the perimeter of the tablet is small in comparison. Thus, the exposed surface of the tablet remains approximately constant during the dissolution process thereby exposing the urea hydrogen peroxide adduct to the aqueous solution at a constant rate. Other geometries which also achieve near constant exposed surface area during dissolution include half hollow spheres and hollow right circular cylinders with length to thickness ratios of 8:1 or greater and large flat slabs with a face surface area to edge surface area ratio of 10:1 or greater. The use of such geometries is included herein by reference to function.

We also discovered that we could control the rate of dissolution of the tablets by mixing distilled water with a solvent such as polyethylene glycol (PEG). By increasing the ratio of PEG to distilled water we can slow down the release of hydrogen peroxide in the solution and set the rate of oxygen production to the specified level.

BRIEF DESCRIPTION OF THE DRAWINGS

The inventive subject matter may best be understood by reference to the following description taken in connection with the accompanying drawings in which.

DETAILED DESCRIPTION

Figure 1:
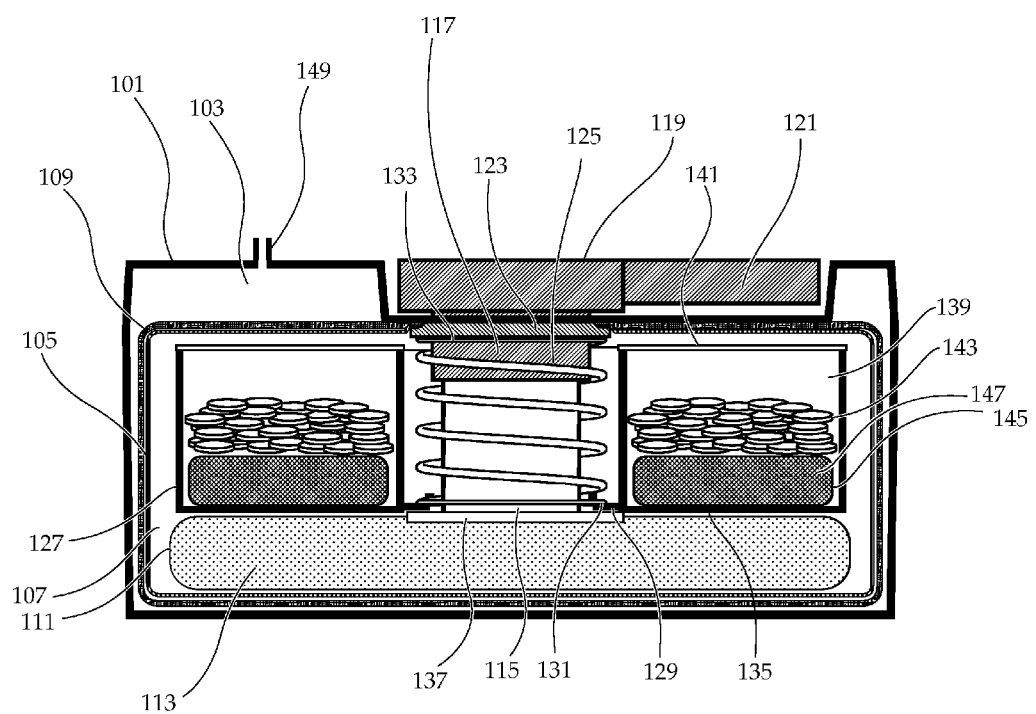
FIG. 1 is a cross-sectional view illustration of an embodiment of the inventive subject matter in an inactive state.

FIG. 1 is an illustration of one embodiment of the inventive subject matter showing a portable chemical oxygen generator prior to activation. The housing 101 contains a reaction chamber 107 and an oxygen accumulation chamber 103. The reaction chamber comprises two compartments; a first compartment 127 containing the controlled-release tablets 143 and multiple PCM packs 145; a second sealed compartment 111 containing a water/catalyst solution 113. In an embodiment of the inventive subject matter, the composition of the controlled-release tablets comprises a urea hydrogen peroxide adduct (UHP). The first compartment 127 has a plurality of holes allowing free movement of fluids. When the controlled release tablets 143 dissolve in water, the UHP adduct releases urea and hydrogen peroxide. The hydrogen peroxide will further decompose to produce water and oxygen in the presence of a suitable catalyst. Many transition metal oxides and their compounds such as manganese dioxide ($MnO_2$) are suitable catalysts for the decomposition of hydrogen peroxide. Due to the reactivity, the water/catalyst solution 113 is separated from the controlled release tablets 143 by storing the water/catalyst mixture in the sealed compartment 111. This sealed compartment is made of water repellent material which is also sturdy enough to withstand shocks and vibration without rupturing. A good example of such material is heavy polyethylene (PE), polyethylene terephthalate (PET) or PE/PET-coated aluminum foil.

It is known that hydrogen peroxide decomposes exothermically into water and oxygen gas. Various means are provided to control the temperature by including heat-absorbing materials in the reaction chamber. In an embodiment of the inventive subject matter, a plurality of PCMs with melting temperatures of between 20° C. and 60° C. degrees and preferably between 25° C. and 50° C. are added inside the first compartment. Such materials can be polymer-encapsulated low melting paraffin waxes or fatty acid esters as found in coconut oil, palm kernel oil, margarines or cocoa butter which will undergo phase change transitions in the range of 20° C. to 60° C. A major advantage of using paraffin waxes and fatty acid esters as heat-absorbing material is that they do not release any gases upon melting unlike inorganic salts which decompose producing carbon dioxide when heated. There are various commercial paraffin waxes that could be used. For example, some of the paraffin waxes made by Mikrotek laboratories (Dayton, Ohio) have melting transitions in the range of 25° C. to 50° C. that could be used in the device. In the embodiment of the inventive subject matter shown in FIG. 1, several PCM packs 145, each containing 50-200 g of a PCM mixture of a paraffin-wax and a fatty acid ester 147 having a melting temperature of 30° C.-50° C., are placed inside and at the bottom of the first compartment 127. As the temperature of the reaction mixture rises to the melting temperature of the PCM, the PCM starts melting and absorbs excess heat. In another embodiment of the inventive subject matter, water can be used instead of a PCM because of its high heat absorption capacity. A mesh 141 sealed on the top of the first compartment 127 maintains the controlled-release tablets 143 and PCM packs 145 inside the first compartment, or 127. The mesh 141 also blocks the movement of the first compartment 127 and of the second sealed compartment 111.

Another aspect of the inventive subject matter is to contain the reaction materials inside the reaction chamber while allowing produced oxygen through using a dual membrane filter. The first membrane 105, made from a hydrophobic material that is resistant to liquids and solids, but permeable to gases. Few materials are both gas permeable and water resistant. In an embodiment of the inventive subject matter, the first membrane is made of a 100% high-density polyethylene material such a Tyvek®. Tyvek® is a commercially available nonwoven fabric from Dupont (Wilmington, Del.) that has moderately high gas permeability and is also highly water resistant. Gas permeability is defined as the airflow in mL/min over a 10 $cm^2$ area according to ISO-5636-3 and referred to as the Bendtsen Air Permeability. A high density polyethylene material such as Tyvek® 1073 or Tyvek® 1059 has a Bendtsen Air Permeability of approximately 600 mL/min. In order to handle the maximum oxygen flow of the device of 6,000 mL/min, there is a need for a membrane surface area of at least 100 $cm^2$ or 16 $in^2$. Water resistance is defined as the height of water column in centimeters that the membrane can withstand without leaking according to DIN EIN 20811 and referred to as the "Hydrostatic Head". In order to prevent a 3 liter aqueous solution from permeating a membrane with a 100 $cm^2$ surface area, the Hydrostatic Head needs to be greater than 30 cm. Tyvek® materials have a typical Hydrostatic Head in excess of 140 cm. Therefore, a first membrane made from such material would allow oxygen gas and water vapor to pass through and would keep the solid and liquid reactants contained in the reaction chamber.

The second membrane 109 between the first membrane 105 and housing 101 is made of a superabsorbent material. By super-absorbent material we mean a hydrophilic material which absorbs and retains aqueous solutions and which, in deionised and distilled water, can absorb up to 800 times its dry weight. The fabric absorbs any unreacted hydrogen peroxide vapor and water vapor and allows high purity oxygen gas to flow through. Preferably, the second membrane is made from melt blown polypropylene produced by Evolution Sorbent Products (Chicago, Ill.). The fabric can also be made from many other materials, such as acrylic fibers, nylon fibers, polyethylene melt blown fibers, or poly(lactic acid) melt blown fibers. Many other synthetic and natural fibers that might be used will occur to those skilled in the art and these are included herein by reference to function. To provide it with its superabsorbent property, the fabric is impregnated with a superabsorbent fiber by needle punching. In an embodiment of the inventive subject matter, superabsorbing polyacrylamide fibers supplied by Technical Absorbents Limited, (Grimsby, United Kingdom) are used as the superabsorbent fiber. When impregnated with an appropriate amount of polyacrylamide fiber, the nonwoven fabric will absorb between 10 and 100 times its own weight in water. Those skilled in the art will recognize that there are other highly absorbent materials that could be substituted for the acrylamide fibers. For example, a corn-derived material called Reon (Absorbent Technologies, Inc., Beaverton, Oreg.), which absorbs nearly 500 times its weight in water, could be needle-punched into the fabric. The fabric is also impregnated with 5-10µ $MnO_2$ powder at a loading of 15 $g/m^2$ by needle punching the powder into the fabric. The incorporation of $MnO_2$ ensures that no hydrogen peroxide vapor can pass through the second membrane together with the produced oxygen gas. Other suitable catalysts for the decomposition of hydrogen peroxide to water and oxygen include transition metal oxides. Other catalysts will occur to those skilled in the art and are included herein by reference to function. The nonwoven fabric serves as a convenient carrier for the superabsorbent fiber and for the $MnO_2$ powder. Importantly, the superabsorbent material should have no volatile contaminants that could find their way into the oxygen stream.

Figure 2:
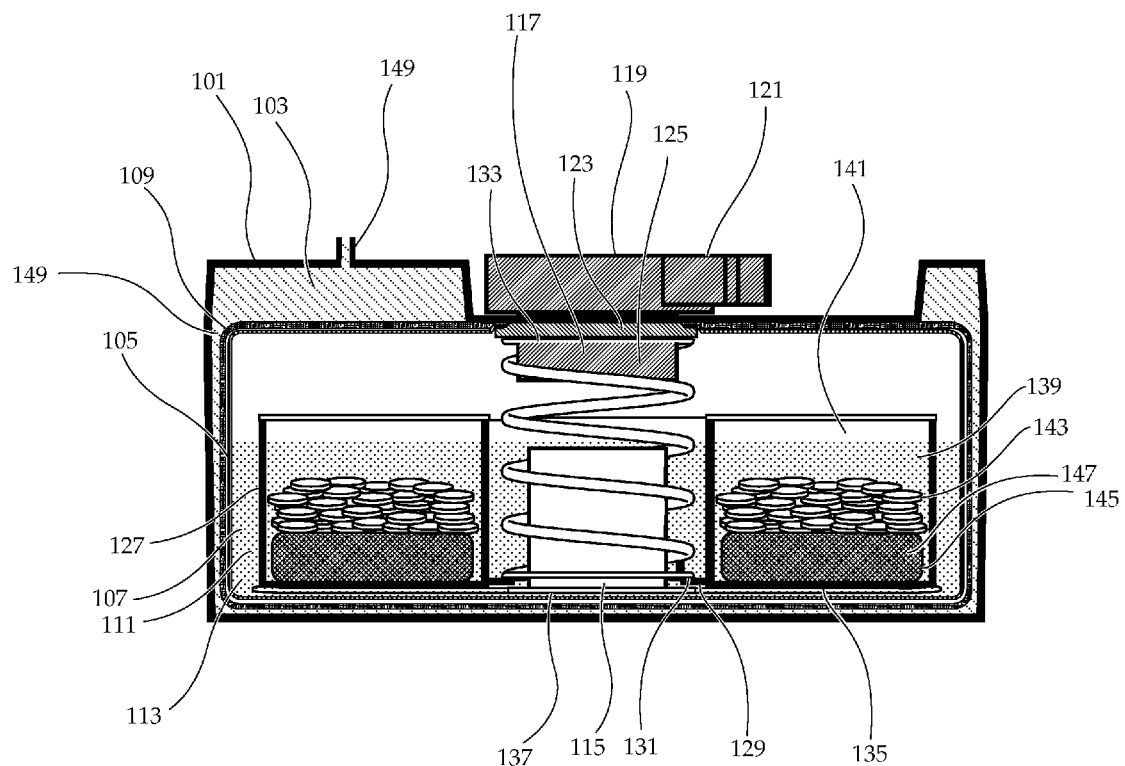
FIG. 2 is a cross-sectional view illustration of an embodiment of the inventive subject matter in an active state.

FIG. 2 is an illustration of the device showing a portable chemical oxygen generator in the active state. A spout 115 of the sealed compartment 111 is disengaged from the release mechanism stem 117. A spring 125 forces the first compartment 127 down against the sealed compartment 111 which becomes compressed between the first compartment 127 and the bottom of the first membrane 105. As a result, most of the water/catalyst solution 113 is forced out through the spout 115 and into the first compartment 127 thereby contacting and immersing the controlled release tablets 143 and PCM packs 145 in the water/catalyst solution 113. Consequently, the controlled release tablets 143 dissolve and oxygen gas is produced. The oxygen gas, water vapor and hydrogen peroxide vapor flow through the first membrane 105, while any solids and liquids remain contained inside the reaction chamber 107. The second membrane 109 absorbs the water and hydrogen peroxide vapors to allow high purity oxygen to flow into the container 103 which is between the housing 101 and the second membrane 109. A flexible tube (not shown) is attached at one end to the outlet 149 of the housing 101 and attached at the other end of the tube to a breathing apparatus (not shown).

Figure 3:
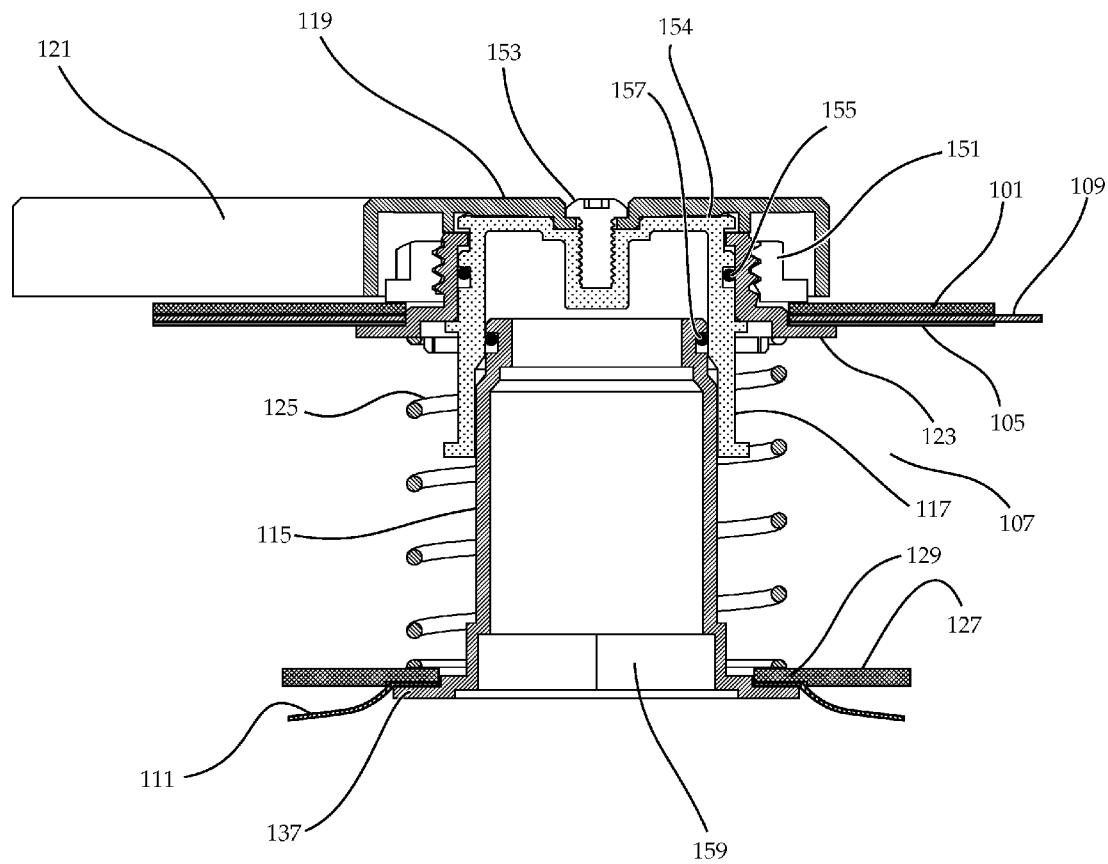
FIG. 3 is an exploded view illustration of an embodiment of a release system of the inventive subject matter.
Figure 4:
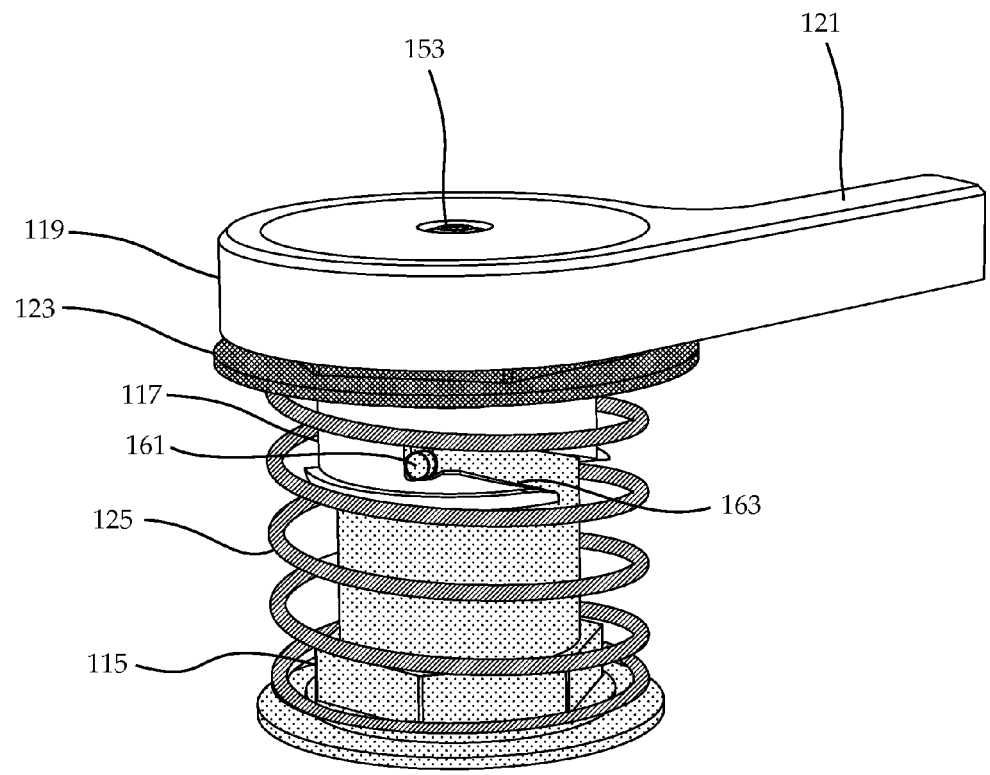
FIG. 4 is an exploded view illustration of an embodiment of a sealing system of the present inventive subject matter.

FIGS. 3 and 4 illustrate the detailed view of the activation mechanism in a embodiment of the inventive subject matter. The activation mechanism is a component of the oxygen generator that initiates the chemical reaction to produce oxygen by releasing the contents of the second compartment into the first compartment. The activation mechanism includes a release knob 119, a handle 121, a release mechanism stem 117, attaching screw 153 and a spring 125. The release knob 119 is located in the center of the top of the housing 101. The attaching screw 153 compresses the release knob 119 against the release mechanism stem 117. There is a fluted bearing surface 154 between the release knob 119 and the release mechanism stem 117 which causes the release mechanism stem 117 to turn with the handle. The first membrane 105, the second membrane 109 and the housing 101 have a circular hole at the top of the membrane, with the holes in alignment and large enough to allow the insertion of the release mechanism stem 117 through the holes. A membrane seal 123 traps the first membrane 105 and second membrane 109 against the housing 101. A sealing nut 151 threads onto the membrane seal 123 to cause it to press against the first membranes 105 and second membrane 109. In addition, an O-ring seal 155 between the release mechanism stem 117 and the membrane seal 123 keeps gas and fluid from escaping the reaction chamber 107 while allowing the release mechanism stem 117 to rotate relative to the membrane seal 123.

The sealed second compartment 111 is connected to a spout 115 which protrudes through the column in the center of the first compartment 127. A hex shaped flange 137 located at the bottom periphery of the spout 115 prevents the first compartment 127 from rotating relative to the spout 115. A retaining boss 161 is located on the top side of the spout 115. Prior to activation of the oxygen generator, the slot 163 on the release mechanism stem 117 captures the retaining boss 161 so that the spout 115 is locked to the release mechanism. The O-ring seal 157 between the release mechanism stem 117 and the spout 115 prevents the water/catalyst solution 113 from escaping into the reaction chamber 107. When the release mechanism stem 117 is twisted onto the spout 115, the spring 125 is compressed and holds the edge of the sealed second compartment 111 firmly between the tray edge 129 and flange 137. This action effectively seals the compartment 111.

To activate the portable chemical oxygen generator, the user turns the release handle 121, causing the release mechanism stem 117 to turn with the handle. The retaining boss 161 is driven down the ramps from the slot 163 and ultimately ejected by the force of the spring 125. The system is now open. The O-ring seal 157 between the spout 115 and the release mechanism stem 117 is disengaged and the water, catalyst and antifoam begin to flow out from the spout 115. When the controlled release tablets come in contact with water, they dissolve slowly and thereby release hydrogen peroxide to the catalyst containing aqueous solution. The reaction temperature is controlled by the sealed PCM packs and the absorption of heat by the aqueous solution. The produced oxygen gas passes through multiple membranes that remove any residual hydrogen peroxide and impurities to yield highly purified breathable oxygen gas at ambient temperature.

Figure 5:
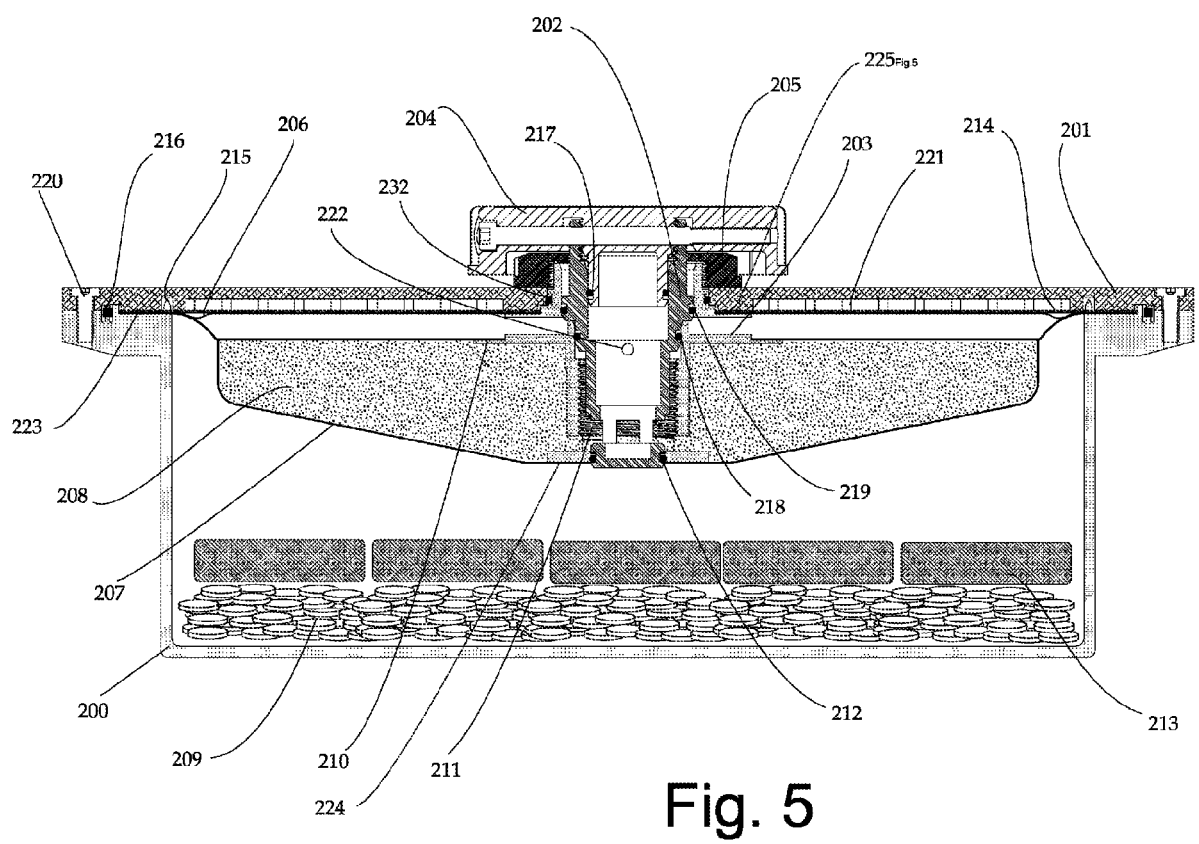
FIG. 5 is a cross-sectional view illustration of another embodiment of the inventive subject matter in an inactive state.

FIG. 5 is an illustration of another embodiment of the inventive subject matter showing a portable chemical oxygen generator prior to activation. The housing comprises a housing bottom 200 and a housing top 201 made from a water repellant material such as polyethylene or polycarbonate. Multiple fasteners 220 hold housing top and housing bottom together. An O-ring 216 seals the contact between the housing top and housing bottom. The activation mechanism comprises a stem 202, valve body 203, knob 204 and locking nut 205. The knob is threaded to the top of the stem. A fastener 226 holds together the knob and the stem and an O-ring 217 provides an airtight seal between the knob and the stem. The valve body is inserted through a circular opening in the housing top and locked in place with the locking nut. The stem is threaded to the valve body via double start threads 211 in the valve body. A lip stop 227 prevents the stem from being pulled out too far. An O-ring 218 provides an airtight seal between the valve body and the stem preventing gas from escaping when the valve is closed. Another O-ring 219 provides an airtight seal between the valve body and the stem preventing gas from escaping the housing.

The chemical reactants comprise oxygen producing controlled-release tablets 209 and an aqueous solution 208. In an embodiment of the inventive subject matter, the tablet composition comprises urea hydrogen peroxide adduct (UHP) as an oxygen producing chemical. Other hydrogen peroxide adducts may also be used. The controlled release tablets are stored in the housing bottom. The water/catalyst mixture is stored in an enclosure 207 made from a liquid impermeable material such as polyethylene. The top of the enclosure is heat sealed to a circular flange 210 of the valve body. The bottom of the container is heat sealed to the bottom 224 of the valve body. Prior to activation, hole 228 is sealed by O-ring 212 between the valve body and the base of the stem, preventing the water/catalyst solution from escaping.

In an embodiment of the inventive subject matter, several sealed PCM packs 213 with a melting temperature in the range between 20° C. and 50° C. degrees are added inside the housing bottom 200. In another embodiment of the inventive subject matter, the PCMs have a melting temperature in the range between 37° C. and 42° C.

Figure 6:
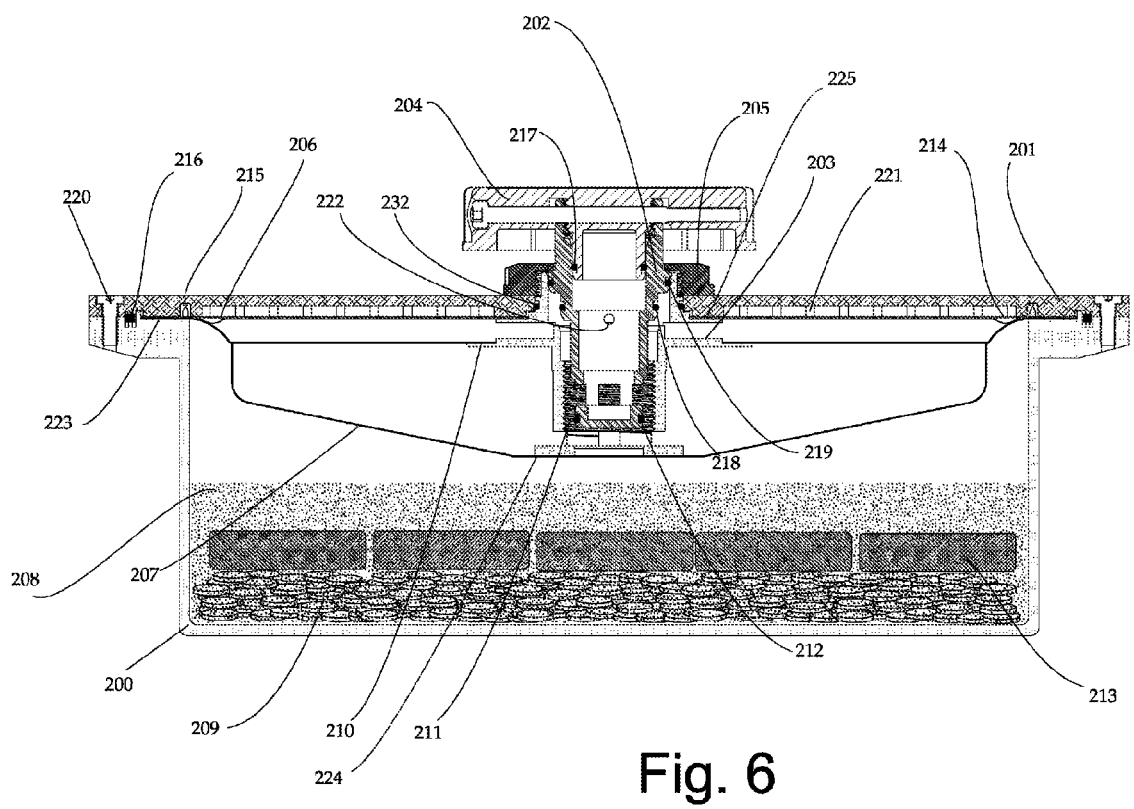
FIG. 6 is a cross-sectional view illustration of another embodiment of the inventive subject matter in an active state.

FIG. 6 is an illustration of another embodiment of the inventive subject matter showing a portable chemical oxygen generator in the active state. In the active state, the aqueous solution 208 contacts and immerses the controlled release tablets 209 and PCM packs 213. Consequently, the controlled-release tablets 208 begin to dissolve releasing hydrogen peroxide which is further decomposed into oxygen gas and water from contact with the catalyst dispersed in the aqueous solution 208.

Figure 7:
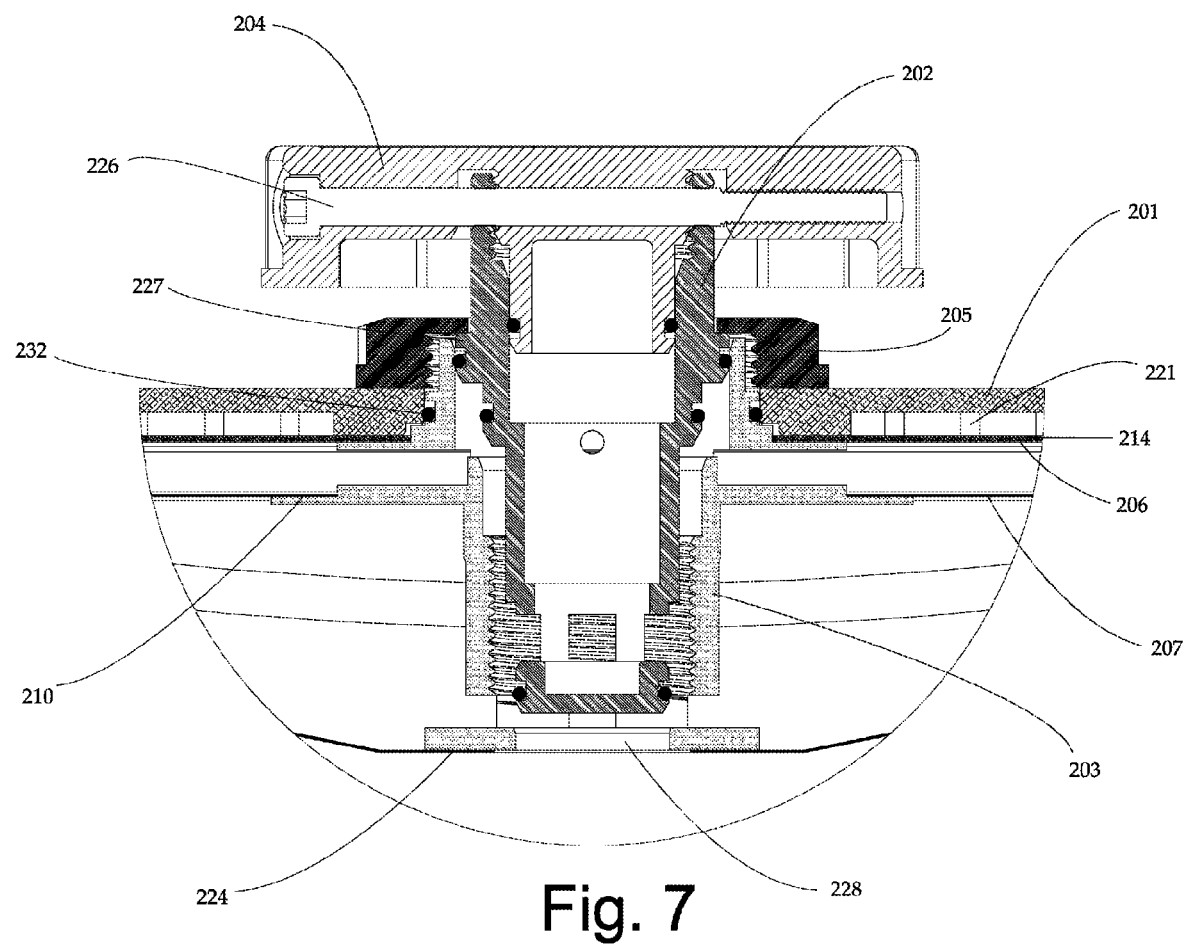
FIG. 7 is an exploded view illustration of another embodiment of a release system of the inventive subject matter.

FIG. 7 is an exploded view of an alternative release mechanism. Turning the knob 204 disengages the O-ring 217 which sealed the contact between the knob 204 and the stem 202, allowing the aqueous solution 208 contained in the enclosure 207 to escape through hole 228 into the housing bottom.

Figure 8:
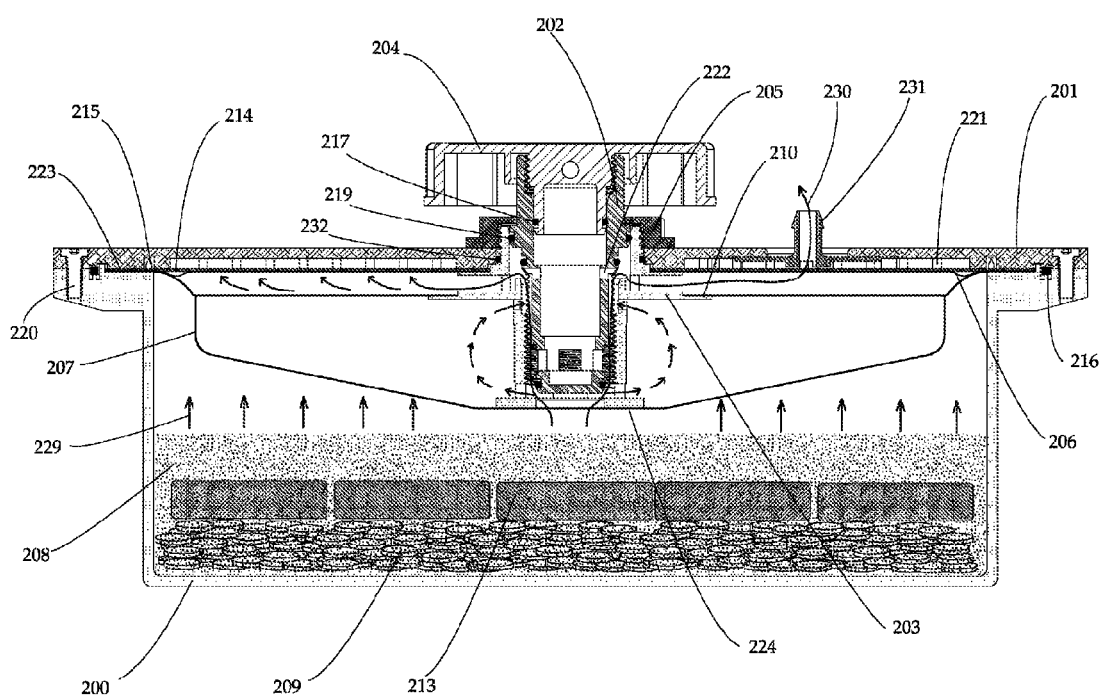
FIG. 8 is a cross sectional view illustration of another embodiment of a sealing system of the inventive subject matter.

FIG. 8 illustrates the oxygen release path through the device. Following contact between the controlled-release tablets and the water/catalyst solution, the oxygen and any water vapor and hydrogen peroxide vapor flow upwards through the hole 228 into the enclosure 207. The oxygen gas as well as any water and hydrogen peroxide vapor will pass through a first membrane 206, made from a hydrophobic material impermeable to liquids and solids and permeable to gases such as Tyvek® made from high density polyethylene. A second membrane 214 between the first membrane and the housing, absorbs any unreacted hydrogen peroxide vapor and water vapor and allows high purity oxygen to flow through. In an embodiment of the inventive subject matter, the second membrane is made from melt blown polypropylene impregnated with superabsorbent polyacrylamide fibers by needle punching. The second membrane is also impregnated with 5-10μ $MnO_2$ powder at a loading of at least 5 g/m$^2$ by needle punching the powder into the fabric. Multiple ribs 221 etched on the inner surface of the top housing provide a tortuous path for the oxygen gas to travel to oxygen outlet 230, thereby cooling the produced oxygen gas.

In an embodiment of the inventive subject matter, the controlled-release tablets are produced from a composition comprising by weight % based on the final tablet weight: from 70% to 99.5% UHP, 36.2% hydrogen peroxide by weight, 0% to 30% crystallized sucrose or other crystallized sugar, 0% to 6% of a gel forming compound, and 0 to 5% of a tablet press release agent. In another embodiment of the inventive subject matter, the tablets comprise by weight % based on the final tablet weight: from 95% to 99.5% UHP, 0% to 5% ground crystallized sucrose or other sugar, 0.5% to 2% of 200 mesh bentonite clay, 0% to 5% of magnesium, aluminum, or calcium stearate, and 0% to 2% mineral oil. Tablet press release agents comprise magnesium stearate and stearic acid and other release agents known to those skilled in the art. The tablets are prepared as flat disks, 1 inch in diameter and ⅛ inch thick. The ingredients are thoroughly mixed and put in the hopper of a Minipress II (SMI Inc., Lebanon, N.J.). Compaction pressure was 455 MN/m².

In another embodiment of the inventive subject matter, the controlled-release tablets are produced from a composition comprising by weight % from 33% to 50% UHP and from 67% to 50% of a hydrophilic compound such as urea. The heat released from the exothermic decomposition of UHP will be in part absorbed by the simultaneous endothermic dissolution of urea in the aqueous solution. The rate of dissolution is further controlled by mixing polyethylene glycol with distilled water in the appropriate ratio in the aqueous solution. The higher the ratio by weight of polyethylene glycol, the slower the rate of dissolution of the tablets and hence the rate of production of oxygen. In another embodiment of the inventive subject matter, the weight % of distilled water to polyethylene glycol in the aqueous solution is between 1:1 and 2:1.

While the inventive subject matter has been described in accordance with certain embodiments, those skilled in the art will understand the many modifications and enhancements which can be made thereto without departing from the true scope and spirit of the inventive subject matter which is limited only by the claims appended below.

Element List First Embodiment

| | |
|---|---|
| 101 | Housing |
| 103 | Oxygen accumulation chamber |
| 105 | First membrane |
| 107 | Reaction chamber |
| 109 | Second membrane |
| 111 | Second sealed compartment |
| 113 | Water/catalyst solution |
| 115 | Spout |
| 117 | Release mechanism stem |
| 119 | Release knob |
| 121 | Handle |
| 123 | Membrane seal |
| 125 | Spring |
| 127 | First compartment |
| 129 | First compartment edge |
| 135 | First compartment bottom |
| 137 | Flange |
| 139 | Second compartment |
| 141 | Second compartment mesh |
| 143 | Controlled release tablets |
| 145 | Heat sealed containers |
| 147 | PCM |
| 149 | Oxygen outlet |
| 151 | Sealing nut |
| 153 | Attaching screw |
| 154 | Fluted surface bearing |
| 155 | O-ring seal |
| 157 | O-ring seal |
| 161 | Retaining boss |
| 163 | Slot |

Element List Second Embodiment

| | |
|---|---|
| 200 | Housing bottom |
| 201 | Housing top |
| 202 | Stem |
| 203 | Valve body |
| 204 | Knob |
| 205 | Locking nut |
| 206 | First membrane |
| 207 | Water/catalyst enclosure |
| 208 | Water and Catalyst mixture |
| 209 | Controlled release tablets |
| 210 | Enclosure sealed to Valve Body |
| 211 | Start threads in Valve Body |
| 212 | O-ring (Stem to Valve Body) |
| 213 | PCM packs |
| 214 | Second membrane |
| 215 | Pin (holds membranes) |
| 216 | O-ring (housing assembly) |
| 217 | O-ring (seals knob and stem) |
| 218 | O-ring (seals stem to valve body) |
| 219 | O-ring (seals stem to valve body) |
| 220 | Fastener (attaches top and bottom housings) |
| 221 | Ribs (create a path for the gas to travel) |
| 222 | Burp hole (Lets air escape from water bag) |
| 223 | Membranes between the two housings |
| 224 | Enclosure heat sealed to Valve Body |
| 225 | Membranes between Valve Body and Housing |
| 226 | Fastener (Holds together the Knob and Stem) |
| 227 | Lip Stop |
| 228 | Hole (Water escape hole) |
| 229 | Oxygen (Resulting from chemical reaction) |
| 230 | Oxygen Path |
| 231 | Oxygen outlet port |
| 232 | O-ring (seals valve Body and housing) |

EXAMPLES

The following non limiting examples illustrate various aspects of the inventive subject matter. Oxygen production rates were measured gravimetrically using a high capacity Ohaus top loading balance with a precision of 0.1 g. A surface mounted thermocouple was taped at the horizontal midpoint of the outer surface of the device about four inches from the bottom. A 4-foot section of silicon tubing was attached to the barbed outlet port of the device to mimic the tubing that connects to a nasal canula. A thermocouple placed about one inch into the outlet of the tubing was used to measure the gas delivery temperature. The flow of oxygen was initiated to rip open the inner water/catalyst bag and thereby deliver the mixture to the tablets. The tear tape was quickly cut off at the gas outlet and the silicon tubing was attached. The weight of the device and the temperatures were recorded at one minute intervals. Volumetric flow rates were computed by numerical differentiation of the weight loss data and applying the ideal gas law to the estimated weight loss rates. Numerical differentiation exacerbates experimental scatter. Thus, weight loss curves are generally more indicative of the constant rates of oxygen production achieved than are the volumetric rates.

Example 1

Purpose: Determine the purity of oxygen generated by a 3 L/min×30 minute device.

Procedure: A device was fabricated to deliver 3 L $O_2$/min for 30 minutes. The oxygen outlet of the device was connected through a one liter low flow reservoir bag via a low flow adaptor air entrainment port to an iVent ventilator (K 052554 7 K 053270, General Electric Company, Schenectady, N.Y.). The iVent ventilator incorporated a Maxtec fuel cell $O_2$ sensor with a digital readout. The outlet loop of the iVent was connected to a one liter "lung" bag and the ventilator was set to deliver a tidal volume of 400 cc at a frequency of 15 with an I:E of 1:2. The iVent received supplemental oxygen from the low flow inlet.

Results: Approximately 1.5 minutes after the device was activated, the FiO2 reading on the iVent display indicated 100% $O_2$. This reading persisted until the $O_2$ supply from the device was exhausted.

Example 2

Purpose: Determine if any hydrogen peroxide residuals were present in the as-delivered oxygen from a 3 L/min×30 minute device.

Procedure: A device was fabricated to deliver 3 L $O_2$/min for 30 minutes. The oxygen produced by the device was bubbled continuously into a beaker containing an acidified 0.02M solution of ferrous ammonium thiocyanate. In the presence of acid, hydrogen peroxide rapidly oxidizes ferrous ion to ferric ion. The ferric ion forms a bright red soluble complex with ammonium thiocyanate. The red complex absorbs strongly in the visible region at 450 nm. Using an absorbance spectrometer to compare the test solution to the as-prepared solution, the presence of hydrogen peroxide can be determined quantitatively to as low as 10 ppm in the oxygen and hydrogen peroxide can be detected at levels of about 1 ppm in the oxygen. A Spec20 digital absorbance spectrometer was used for the measurements.

Results: Comparison of the test solution to the as-prepared stock solution indicated no observable residual hydrogen peroxide had entered the test solution. The level of residual hydrogen peroxide was below the detection limit of the analysis method (~1 ppm).

Example 3

Evaluation of Levels of Volatile Organic Compounds (VOCs) in the Oxygen Produced by a 6 L/min×15 Minute Predicate Device Procedure: A device was constructed as above. Activated carbon powder (Fischer Scientific) was added to the superabsorbent fabric barrier by needle punching at a coverage of 15 g/m². The device utilized Pluronic L-81 (BASF) as an antifoam. L-81 is a PEO-PPO-PEO triblock poloxamer and, like most polymers, is expected to carry some low level of volatile residuals. For example, in headspace GC tests, this poloxamer was found to contain low levels of acetaldehyde. To counter the potential for such residuals to enter the oxygen stream, activated carbon powder was added to the fabric to adsorb any residual VOCs in the oxygen as it passed through the barrier.

After the device was activated, oxygen was allowed to flow for two minutes after initial inflation of the device. The outlet gas tubing was then connected to a fresh Tedlar gas sampling bag, the valve on the Tedlar bag was opened, and gas allowed to inflate the Tedlar bag to approximately ⅔ of its capacity. The valve on the Tedlar bag was then closed and the bag was disconnected from the device. The gas outlet tubing from the device was immediately connected to a second fresh Tedlar gas sampling bag. The second bag was filled and disconnected as before. A third Tedlar bag was filled with air from the laboratory using a standard laboratory rubber hand bulb as a pump. The bags were shipped to ALS Laboratories (Cincinnati, Ohio) for analysis.

Results: The ALS findings are summarized in Table 3.

TABLE 3

Summary of TO-15 VOC findings.

| VOC ID | Concentration, ppbv | | |
|---|---|---|---|
| | Sample 1 | Sample 2 | Lab Air |
| 2-propanol (isopropyl alcohol) | 260 | 58 | 65 |
| acetone | 64 | 49 | 660 |
| methylene chloride | 1500 | 1300 | 5700 |
| propene (propylene monomer[a]) | 96 | 110 | ND |
| trichlorofluoromethane (Freon-11, F-11) | 46 | 41 | 500 |

TABLE 3-continued

Summary of TO-15 VOC findings.

| VOC ID | Concentration, ppbv | | |
|---|---|---|---|
| | Sample 1 | Sample 2 | Lab Air |
| 1,1-dichloroethene (vinylidene chloride monomer[b]) | ND | ND | 15 |
| toluene | ND | ND | 18 |
| trans-1,2-dichloroethene | ND | ND | 10 |

[a]Propylene is the monomer used to produce polypropylene.
[b]Vinylidene chloride is the monomer used to produce polyvinylidene chloride (Saran Wrap).

With the exception of propylene, all of the VOCs found in the oxygen samples appear in the laboratory air sample. Propylene, is the monomer used to manufacture polypropylene. This polymer was used to produce the nonwoven fabric that made up the bulk of the superabsorbent barrier in the device. Low levels of residual monomers are common in most polymers so finding propylene in oxygen that passed through the superabsorbent is not surprising. At a concentration of about 100 ppbv (0.1 ppmv), the amount of propylene in the gas is more than an order of magnitude less than the TEEL-0 value assigned for propylene by the U.S. Department of Energy, 12.5 mg/m³ (about 6.7 ppmv). The TEEL-0 value is defined as the threshold concentration below which most people will experience no adverse health effects. No other VOCs appeared in the delivered oxygen. The results verify the efficacy of powdered carbon as an adsorbent for VOCs in oxygen-producing devices.

Example 4

Purpose: Measure rates of oxygen production and temperatures for a 6 L/min×15 minute device design.

| Flow rate | Water | UHP Tablets | Powder | PDMS | $MnO_2$ (Colloidal) | $MnO_2$ (Powder) | PCM |
|---|---|---|---|---|---|---|---|
| 6 L/min | 1800 mL | 900 g | 1.5 g | 180 g | 600 g | 60 g | 100 g |

Results: Data taken during the test are recorded in Table 4.

TABLE 4

104 L Configuration 6 L/min

| t, min | Q, SLPM | Wt, g | Loss, g | T, °C. (bag) | T, °C. (gas) | L @ 22° C. | ΔW/Δt, g/min |
|---|---|---|---|---|---|---|---|
| 0 | 0.0 | 4314.6 | 0.0 | 23.1 | 23.1 | 0.0 | 0.00 |
| 1 | 7.9 | 4303.2 | 11.4 | 26.0 | 23.2 | 8.6 | 10.30 |
| 2 | 6.6 | 4294.0 | 20.6 | 29.7 | 23.4 | 15.6 | 8.45 |
| 3 | 6.0 | 4286.3 | 28.3 | 30.7 | 23.3 | 21.4 | 7.70 |
| 4 | 6.0 | 4278.6 | 36.0 | 32.1 | 23.3 | 27.2 | 7.70 |
| 5 | 6.0 | 4270.9 | 43.7 | 32.8 | 23.4 | 33.1 | 7.70 |
| 6 | 6.1 | 4263.2 | 51.4 | 34.4 | 23.6 | 38.9 | 7.70 |
| 7 | 6.1 | 4255.5 | 59.1 | 35.6 | 23.5 | 44.7 | 7.70 |
| 8 | 6.1 | 4247.8 | 66.8 | 37.0 | 23.6 | 50.5 | 7.70 |
| 9 | 6.1 | 4240.1 | 74.5 | 38.1 | 24.0 | 56.3 | 7.70 |
| 10 | 6.2 | 4232.4 | 82.2 | 39.4 | 25.1 | 62.2 | 7.70 |
| 11 | 6.1 | 4224.7 | 89.9 | 38.5 | 25.1 | 68.0 | 7.70 |
| 12 | 6.2 | 4217.0 | 97.6 | 41.4 | 25.5 | 73.8 | 7.65 |
| 13 | 6.1 | 4209.4 | 105.2 | 42.2 | 25.6 | 79.6 | 7.55 |
| 14 | 6.0 | 4201.9 | 112.7 | 42.2 | 25.6 | 85.2 | 7.45 |
| 15 | 5.9 | 4194.5 | 120.1 | 41.4 | 25.5 | 90.8 | 7.35 |
| 16 | 4.7 | 4187.2 | 127.4 | 39.8 | 25.2 | 96.4 | 5.80 |
| 17 | 3.0 | 4182.9 | 131.7 | 38.5 | 25.1 | 99.6 | 3.70 |

TABLE 4-continued

104 L Configuration 6 L/min

| t, min | Q, SLPM | Wt, g | Loss, g | T, °C. (bag) | T, °C. (gas) | L @ 22° C. | ΔW/Δt, g/min |
|---|---|---|---|---|---|---|---|
| 18 | 2.0 | 4179.8 | 134.8 | 37.3 | 24.0 | 102.0 | 2.55 |
| 19 | 1.0 | 4177.8 | 136.8 | 36.2 | 23.8 | 103.5 | 1.30 |
| 20 | 0.2 | 4177.2 | 137.4 | 33.0 | 23.5 | 103.9 | 0.30 |

Example 5

Purpose: Rates of oxygen production for a 3 L/min device design.

| Flow rate | Water | Tablets | UHP Powder | PDMS | $MnO_2$ (Colloidal) | $MnO_2$ (Powder) | PCM |
|---|---|---|---|---|---|---|---|
| 3 L/min | 1400 mL | 1114 g | 2 g | 60 g | 600 g | 60 g | 200 g |

Results: Data taken during the test are recorded in Table 5.

TABLE 5

90 L Configuration 3 L/min

| t, min | Q, SLPM | Wt, g | Loss, g | T, °C. (bag) | T, °C. (gas) | L @ 22° C. | ΔW/Δt, g/min |
|---|---|---|---|---|---|---|---|
| 0 | 0 | 3974.5 | 0.0 | 24.5 | 23.9 | 0 | 3.6 |
| 1 | 2.7 | 3970.3 | 4.2 | 24.1 | 23.9 | 3.18 | 3.6 |
| 2 | 2.7 | 3966.6 | 7.9 | 25.1 | 23.9 | 5.97 | 3.6 |
| 3 | 2.7 | 3963.4 | 11.1 | 25.4 | 24.0 | 8.40 | 3.6 |
| 4 | 2.8 | 3960.2 | 14.3 | 25.2 | 24.0 | 10.82 | 3.7 |
| 5 | 2.8 | 3956.0 | 18.5 | 25.2 | 24.0 | 13.99 | 3.7 |
| 6 | 2.8 | 3952.8 | 21.7 | 25.2 | 23.9 | 16.41 | 3.7 |
| 7 | 2.8 | 3948.1 | 26.4 | 25.5 | 23.9 | 19.97 | 3.7 |
| 8 | 2.9 | 3945.4 | 29.1 | 25.7 | 23.9 | 22.01 | 3.8 |
| 9 | 2.9 | 3941.7 | 32.8 | 26.0 | 23.9 | 24.81 | 3.7 |
| 10 | 3.0 | 3937.5 | 37.0 | 26.0 | 23.9 | 27.98 | 3.9 |
| 11 | 3.0 | 3933.3 | 41.2 | 26.4 | 23.9 | 31.16 | 3.9 |
| 12 | 2.8 | 3930.1 | 44.4 | 27.0 | 24.0 | 33.58 | 3.6 |
| 13 | 2.8 | 3925.9 | 48.6 | 27.4 | 24.1 | 36.76 | 3.7 |
| 14 | 2.9 | 3922.2 | 52.3 | 27.6 | 24.0 | 39.56 | 3.7 |
| 15 | 2.8 | 3919.5 | 55.0 | 27.7 | 24.2 | 41.60 | 3.7 |
| 16 | 2.9 | 3914.8 | 59.7 | 28.1 | 24.2 | 45.15 | 3.7 |
| 17 | 2.9 | 3911.1 | 63.4 | 28.6 | 24.2 | 47.95 | 3.8 |
| 18 | 2.7 | 3907.9 | 66.6 | 28.9 | 24.3 | 50.37 | 3.5 |
| 19 | 2.8 | 3903.7 | 70.8 | 29.5 | 24.3 | 53.55 | 3.6 |
| 20 | 2.9 | 3900.5 | 74.0 | 29.5 | 24.3 | 55.97 | 3.7 |
| 21 | 2.8 | 3897.3 | 77.2 | 30.2 | 24.4 | 58.39 | 3.6 |
| 22 | 2.8 | 3893.1 | 81.4 | 30.2 | 24.4 | 61.56 | 3.6 |
| 23 | 2.8 | 3888.9 | 85.6 | 30.4 | 24.3 | 64.74 | 3.6 |
| 24 | 2.8 | 3886.2 | 88.3 | 30.9 | 24.4 | 66.78 | 3.6 |
| 25 | 2.9 | 3882.5 | 92.0 | 31.1 | 24.5 | 69.58 | 3.7 |
| 26 | 3.0 | 3878.8 | 95.7 | 31.3 | 24.5 | 72.38 | 3.8 |
| 27 | 2.9 | 3874.6 | 99.9 | 31.4 | 24.4 | 75.56 | 3.7 |
| 28 | 2.9 | 3870.4 | 104.1 | 31.6 | 24.4 | 78.73 | 3.7 |
| 29 | 2.6 | 3867.7 | 106.8 | 31.9 | 24.5 | 80.78 | 3.3 |
| 30 | 2.3 | 3864.0 | 110.5 | 31.9 | 24.3 | 83.57 | 3.0 |

Example 6

Rates of Oxygen Production for a 0.5 L/min Device Design

| Flow rate | Water | Tablets | UHP Powder | PDMS | $MnO_2$ (Colloidal) | $MnO_2$ (Powder) | PCM |
|---|---|---|---|---|---|---|---|
| 0.5 L/min | 680 mL | 340 g | 1 g | 68 g | 227 g | 23 g | 50 g |

Results: Data taken during the test are recorded in Table 6.

TABLE 6

30 L Configuration 0.5 L/min

| t, min | Q, SLPM | Wt, g | Loss, g | T, °C. (bag) | T, °C. (gas) | L @ 22° C. | ΔW/Δt, g/min |
|---|---|---|---|---|---|---|---|
| 0 | 0 | 1611.0 | 0 | 25.1 | 24.9 | 0 | 0.6 |
| 2 | 0.49 | 1609.5 | 1.5 | 24.9 | 24.6 | 1.13 | 0.6 |
| 4 | 0.49 | 1608.3 | 2.7 | 24.7 | 25.7 | 2.04 | 0.6 |
| 6 | 0.49 | 1607.1 | 3.9 | 24.9 | 25.6 | 2.95 | 0.6 |
| 8 | 0.50 | 1605.9 | 5.1 | 24.8 | 25.2 | 3.86 | 0.7 |
| 10 | 0.51 | 1604.5 | 6.5 | 25.0 | 25.0 | 4.92 | 0.7 |
| 12 | 0.51 | 1603.2 | 7.8 | 24.8 | 24.6 | 5.90 | 0.7 |
| 14 | 0.51 | 1601.7 | 9.3 | 24.4 | 24.4 | 7.03 | 0.7 |
| 16 | 0.51 | 1600.6 | 10.4 | 24.6 | 24.3 | 7.87 | 0.7 |
| 18 | 0.50 | 1599.1 | 11.9 | 24.5 | 24.2 | 9.00 | 0.7 |
| 20 | 0.50 | 1597.9 | 13.1 | 24.6 | 24.2 | 9.91 | 0.7 |
| 22 | 0.49 | 1596.5 | 14.5 | 24.6 | 24.2 | 10.97 | 0.6 |
| 24 | 0.48 | 1595.3 | 15.7 | 24.9 | 24.2 | 11.87 | 0.6 |
| 26 | 0.48 | 1593.9 | 17.1 | 24.2 | 24.9 | 12.93 | 0.6 |
| 28 | 0.49 | 1592.7 | 18.3 | 24.2 | 24.9 | 13.84 | 0.6 |
| 30 | 0.50 | 1591.7 | 19.3 | 24.1 | 25.0 | 14.60 | 0.7 |
| 32 | 0.49 | 1590.1 | 20.9 | 24.2 | 25.2 | 15.81 | 0.6 |
| 34 | 0.50 | 1588.7 | 22.3 | 24.2 | 25.3 | 16.87 | 0.7 |
| 36 | 0.47 | 1587.5 | 23.5 | 24.2 | 25.2 | 17.77 | 0.6 |
| 38 | 0.48 | 1586.5 | 24.5 | 24.2 | 25.3 | 18.53 | 0.6 |
| 40 | 0.49 | 1585.0 | 26 | 24.2 | 25.2 | 19.66 | 0.6 |
| 42 | 0.50 | 1583.9 | 27.1 | 24.1 | 25.3 | 20.50 | 0.7 |
| 44 | 0.51 | 1582.4 | 28.6 | 24.1 | 25.3 | 21.63 | 0.7 |
| 46 | 0.52 | 1581.1 | 29.9 | 24.0 | 25.4 | 22.61 | 0.7 |
| 48 | 0.49 | 1579.9 | 31.1 | 24.1 | 25.5 | 23.52 | 0.6 |
| 50 | 0.49 | 1578.3 | 32.7 | 24.0 | 25.5 | 24.73 | 0.6 |
| 52 | 0.50 | 1577.1 | 33.9 | 24.0 | 25.7 | 25.64 | 0.7 |
| 54 | 0.48 | 1576.1 | 34.9 | 24.0 | 25.5 | 26.40 | 0.6 |
| 56 | 0.49 | 1574.7 | 36.3 | 24.0 | 25.7 | 27.45 | 0.6 |
| 58 | 0.46 | 1573.1 | 37.9 | 24.0 | 25.8 | 28.66 | 0.6 |
| 60 | 0.42 | 1572.1 | 38.9 | 24.0 | 25.6 | 29.42 | 0.5 |

Example 7

Zero Order Release Potential of Clay-Containing Tablets

Procedure: Tablets (23 mm diameter×3 mm thick, ~2 g each) were formulated to contain 79.5 wt % UHP, 10 wt % crystallized sucrose, 10 wt % 200 mesh bentonite clay powder, and 0.5 wt % mineral oil. 15 grams of tablets were contacted with 30 g of water containing 0.075 g of colloidal $MnO_2$. For this formulation, no powdered $MnO_2$ was used and no antifoam was used. The vessel containing the mixture was weighed continuously and the weight recorded with time. The gas from the vessel was passed through a layer of rapidly absorbing silica gel to prevent moisture escape from affecting the weight measurements.

Results: The table below shows the weight loss due to oxygen production versus time. The tablet weight loss per minute and oxygen produced per minute was essentially constant for the first 30 minutes of the reaction and dropped rapidly thereafter. A total weight loss of 1.94 g was measured compared to a theoretical loss of 2.04 g based on the presumed 98% purity of the UHP. The linearity of the data and the visually observed slow dissolution of the tablets from the surfaces only confirmed the zero order release of the formulation

TABLE 7

Zero-Order Release Tablets

| t, min | Q, SLPM | Wt, g | Loss, g | T, °C | S Liters | ΔW/Δt, g/min |
|---|---|---|---|---|---|---|
| 0.0 | 0.000 | 140.04 | 0 | 20.5 | 0 | 0 |
| 2.0 | 0.032 | 139.92 | 0.12 | 19.5 | 0.08 | 0.045 |
| 4.0 | 0.030 | 139.84 | 0.2 | 20.3 | 0.14 | 0.044 |
| 6.0 | 0.030 | 139.74 | 0.3 | 21.4 | 0.21 | 0.044 |
| 8.0 | 0.030 | 139.66 | 0.38 | 22.5 | 0.27 | 0.044 |
| 10.0 | 0.031 | 139.58 | 0.46 | 23.5 | 0.32 | 0.044 |
| 12.0 | 0.030 | 139.48 | 0.56 | 24.4 | 0.39 | 0.044 |
| 14.0 | 0.031 | 139.4 | 0.64 | 25.6 | 0.45 | 0.044 |
| 16.0 | 0.031 | 139.31 | 0.73 | 27.3 | 0.51 | 0.045 |
| 18.0 | 0.031 | 139.22 | 0.82 | 29.1 | 0.57 | 0.044 |
| 20.0 | 0.032 | 139.13 | 0.91 | 30.6 | 0.64 | 0.046 |
| 22.0 | 0.032 | 139.04 | 1 | 32.1 | 0.70 | 0.046 |
| 24.0 | 0.033 | 138.95 | 1.09 | 33.5 | 0.76 | 0.047 |
| 26.0 | 0.033 | 138.85 | 1.19 | 34.8 | 0.83 | 0.047 |
| 28.0 | 0.033 | 138.75 | 1.29 | 36.2 | 0.90 | 0.047 |
| 30.0 | 0.031 | 138.66 | 1.38 | 37.7 | 0.97 | 0.045 |
| 32.0 | 0.028 | 138.57 | 1.47 | 38.9 | 1.03 | 0.041 |
| 34.0 | 0.026 | 138.48 | 1.56 | 39.7 | 1.09 | 0.037 |
| 36.0 | 0.023 | 138.42 | 1.62 | 40 | 1.13 | 0.032 |
| 38.0 | 0.019 | 138.37 | 1.67 | 40.4 | 1.17 | 0.028 |
| 40.0 | 0.016 | 138.3 | 1.74 | 40.5 | 1.22 | 0.023 |
| 42.0 | 0.013 | 138.27 | 1.77 | 40.4 | 1.24 | 0.019 |
| 44.0 | 0.011 | 138.23 | 1.81 | 40.3 | 1.27 | 0.016 |
| 46.0 | 0.009 | 138.21 | 1.83 | 40 | 1.28 | 0.013 |
| 48.0 | 0.007 | 138.19 | 1.85 | 39.6 | 1.29 | 0.011 |
| 50.0 | 0.006 | 138.16 | 1.88 | 39.1 | 1.32 | 0.009 |
| 52.0 | 0.005 | 138.15 | 1.89 | 38.5 | 1.32 | 0.007 |
| 54.0 | 0.005 | 138.14 | 1.9 | 36.3 | 1.33 | 0.007 |
| 56.0 | 0.005 | 138.13 | 1.91 | 36.1 | 1.34 | 0.007 |
| 58.0 | 0.005 | 138.12 | 1.92 | 35.6 | 1.34 | 0.007 |
| 60.0 | 0.005 | 138.1 | 1.94 | 35 | 1.36 | 0.007 |

Example 8

Urea/UHP Controlled Release Tablets

Procedure: Tablets (23 mm diameter×3 mm thick, ~2 g each) were formulated to contain 46.3 wt % UHP, 53.7 wt % urea. 1127.6 grams of tablets were contacted with 872 g of a 50% distilled water/50% polyethylene glycol solution. For this formulation, 160 g of powdered $MnO_2$ dispersed in the solution was used as catalyst. The vessel containing the mixture was weighed continuously and the weight recorded with time. The gas from the vessel was passed through a layer of rapidly absorbing silica gel to prevent moisture escape from affecting the weight measurements.

Results: Table 8 below shows the weight loss due to oxygen production versus time. The reaction produced an essentially constant 2 liters of oxygen per minute. The endothermic dissolution of the urea in the distilled water/PEG solution absorbed part of the heat produced from the decomposition of the hydrogen peroxide into oxygen and mitigated the rise of the temperature of the produced oxygen which never exceeded 45° C. inside the reaction chamber and 35° C. outside the reaction chamber.

TABLE 8

Urea/UHP Controlled release tablets

| t, min | Q, SLPM | Wt, g | T (in), °C | T (out), °C | Fract. Loss | S Liters | ΔW/Δt, g/min |
|---|---|---|---|---|---|---|---|
| 0 | 0.000 | 3995.1 | 21.8 | 22.2 | 0 | 0 | 0 |
| 1 | 2.100 | 3992.1 | 17.8 | 22.2 | 0.032 | 2.100 | 3.000 |
| 2 | 2.065 | 3989.1 | 17.3 | 22.3 | 0.063 | 4.200 | 2.950 |
| 3 | 1.890 | 3986.2 | 17.4 | 22.4 | 0.094 | 6.230 | 2.700 |
| 4 | 1.820 | 3983.7 | 17.8 | 22.5 | 0.121 | 7.979 | 2.600 |
| 5 | 1.855 | 3981.0 | 18.6 | 22.7 | 0.149 | 9.869 | 2.650 |
| 6 | 1.750 | 3978.4 | 19.0 | 23.1 | 0.177 | 11.689 | 2.500 |
| 7 | 1.750 | 3976.0 | 18.8 | 23.4 | 0.202 | 13.369 | 2.500 |
| 8 | 1.785 | 3973.4 | 18.7 | 23.6 | 0.229 | 15.189 | 2.550 |
| 9 | 1.785 | 3970.9 | 18.2 | 23.9 | 0.256 | 16.939 | 2.550 |
| 10 | 1.890 | 3968.3 | 18.2 | 24.1 | 0.283 | 18.759 | 2.700 |
| 11 | 1.855 | 3965.5 | 18.4 | 24.4 | 0.313 | 20.718 | 2.650 |
| 12 | 1.855 | 3963.0 | 19.0 | 24.7 | 0.339 | 22.468 | 2.650 |
| 13 | 1.925 | 3960.2 | 19.6 | 25.2 | 0.369 | 24.428 | 2.750 |
| 14 | 1.960 | 3957.5 | 20.3 | 25.6 | 0.398 | 26.318 | 2.800 |
| 15 | 2.065 | 3954.6 | 21.1 | 25.9 | 0.428 | 28.348 | 2.950 |
| 16 | 2.100 | 3951.6 | 21.7 | 26.4 | 0.460 | 30.448 | 3.000 |
| 17 | 2.135 | 3948.6 | 23.6 | 26.8 | 0.492 | 32.548 | 3.050 |
| 18 | 2.205 | 3945.5 | 25.8 | 27.4 | 0.525 | 34.717 | 3.150 |
| 19 | 2.205 | 3942.3 | 27.8 | 28.0 | 0.558 | 36.957 | 3.150 |
| 20 | 2.205 | 3939.2 | 29.3 | 28.6 | 0.591 | 39.127 | 3.150 |
| 21 | 2.275 | 3936.0 | 30.9 | 29.3 | 0.625 | 41.367 | 3.250 |
| 22 | 2.450 | 3932.7 | 32.7 | 30.0 | 0.660 | 43.677 | 3.500 |
| 23 | 2.205 | 3929.0 | 34.2 | 30.8 | 0.699 | 46.266 | 3.150 |
| 24 | 1.925 | 3926.4 | 36.8 | 31.5 | 0.727 | 48.086 | 2.750 |
| 25 | 1.995 | 3923.5 | 37.9 | 31.9 | 0.757 | 50.116 | 2.850 |
| 26 | 1.960 | 3920.7 | 38.4 | 32.5 | 0.787 | 52.076 | 2.800 |
| 27 | 1.785 | 3917.9 | 39.7 | 33.2 | 0.816 | 54.036 | 2.550 |
| 28 | 1.610 | 3915.6 | 41.0 | 33.8 | 0.841 | 55.646 | 2.300 |
| 29 | 1.610 | 3913.3 | 43.4 | 34.4 | 0.865 | 57.256 | 2.300 |
| 30 | 1.610 | 3911.0 | 44.3 | 34.9 | 0.889 | 58.866 | 2.300 |

What is claimed is:

1. A portable chemical oxygen generator comprising:
a housing enclosing a reaction chamber comprising a first compartment containing an oxygen generating composition comprising a hydrogen peroxide adduct and a temperature stabilizing material formulated into controlled-release tablets and a second sealed compartment containing a catalyst dispersed in an aqueous solution;
activation means attached to the housing for opening the second sealed compartment and for immersing the controlled-release tablets in the aqueous solution;
a dual membrane filter comprising a first membrane made of a gas permeable and hydrophobic material with a Bendtsen Air Permeability of at least 300 mL/min and a Hydrostatic Head of at least 30 cm $H_2O$, said first membrane letting oxygen and water and hydrogen peroxide vapors pass through while retaining the oxygen generating composition and the aqueous solution and a second membrane made of a hydrophilic superabsorbent material impregnated with catalyst particles at a loading greater than 5 $g/m^2$, said second membrane letting oxygen through while decomposing and absorbing residual hydrogen peroxide vapor.

2. The generator of claim 1 wherein the hydrogen peroxide adduct is UHP.

3. The generator of claim 2 wherein the catalyst is a transition metal oxide colloid.

4. The Generator of claim 1 wherein the first membrane is made of high-density polyethylene.

5. The generator of claim 4 wherein the second membrane is made of a nonwoven fabric needle-punched with superabsorbent polyacrylamide fibers, said second membrane being capable of absorbing and retaining between 10 and 100 times its own weight in water.

6. A portable chemical oxygen generator comprising:

a housing enclosing a reaction chamber comprising a first compartment containing an oxygen generating composition comprising a hydrogen peroxide adduct and a temperature stabilizing material comprising a hydrophilic compound producing an endothermic reaction upon dissolution in water, said oxygen generating composition formulated into controlled-release tablets comprising by weight % from 33% to 50% UHP and from 67% to 50% urea to maintain the temperature of the reaction chamber at a level lower than 45° C., and a second sealed compartment made from a liquid impermeable material containing a catalyst dispersed in an aqueous solution;

activation means attached to the housing for opening the second sealed compartment and for immersing the controlled-release tablets in the aqueous solution;

a dual membrane filter comprising a first membrane made of a gas permeable and hydrophobic material and a second membrane made of a hydrophilic material impregnated with catalyst particles.

7. The generator of claim 6 wherein the temperature stabilizing material has an enthalpy of solution greater than 50 cal/g.

8. The generator of claim 7 wherein the temperature stabilizing material is urea.

9. A portable chemical oxygen generator comprising:

a housing enclosing a reaction chamber comprising a first compartment containing an oxygen generating composition comprising a hydrogen peroxide adduct and a temperature stabilizing material formulated into controlled-release tablets, and a second sealed compartment made from a liquid impermeable material containing a catalyst dispersed in an aqueous solution, said controlled-release tablets having a ratio of tablet length to tablet thickness greater than 8:1 to produce a zero-order release rate of oxygen over a period of time greater than 30 minutes;

activation means attached to the housing for immersing the controlled-release tablets in the aqueous solution;

a dual membrane filter comprised of a first membrane made of a gas permeable and hydrophobic material and a second membrane made of a hydrophilic material impregnated with catalyst particles.

10. The generator of claim 9 wherein the aqueous solution comprises distilled water and polyethylene glycol.

11. The generator of claim 9 wherein the oxygen generating composition comprises a slowly dissolving hydrophobic binder.

12. The generator of claim 11 where the binder is crystallized sucrose.

* * * * *